US008661421B2

(12) United States Patent (10) Patent No.: US 8,661,421 B2
Domeika et al. (45) Date of Patent: Feb. 25, 2014

(54) METHODS AND APPARATUSES FOR ENDIAN CONVERSION

(75) Inventors: Maximillian J. Domeika, Sherwood, OR (US); Hugh Wilkinson, Newton, MA (US); Michael P. Rice, Beaverton, OR (US)

(73) Assignee: Intel Corporation, Santa Clara, CA (US)

(*) Notice: Subject to any disclaimer, the term of this patent is extended or adjusted under 35 U.S.C. 154(b) by 1100 days.

(21) Appl. No.: 12/643,006

(22) Filed: Dec. 21, 2009

(65) Prior Publication Data

US 2011/0154306 A1 Jun. 23, 2011

(51) Int. Cl.
*G06F 9/45* (2006.01)

(52) U.S. Cl.
USPC .......................................................... 717/141

(58) Field of Classification Search
USPC ................................. 717/124–133, 140–144
See application file for complete search history.

(56) References Cited

U.S. PATENT DOCUMENTS

| 6,772,320 | B1 | 8/2004 | Raj |
| 7,552,427 | B2 | 6/2009 | Adiletta et al. |
| 2009/0222800 | A1 | 9/2009 | Adiletta et al. |

FOREIGN PATENT DOCUMENTS

JP 05-119960 5/1993

OTHER PUBLICATIONS

Intel, "Intel® Fortran Compiler User's Guide", 2002, Intel Corporation, 285 pages.*
The Portland Group, "PGI® User's Guide", 2007, The Portland Group™ and STMicroelectronics, Chapter 1 to Chapter 15, pp. 1-242.*
European Patent Office, Communication Pursuant to Article 94(3) EPC mailed Jul. 21, 2011 in European application No. 10 252 182.0-1243.
Japanese Patent Office, Notice of Reasons for Rejection mailed Jul. 31, 2012 in Japanese application No. 2010247123.
U.S. Appl. No. 12/643,216, filed Dec. 21, 2009, entitled "Endian Conversion Tool," by Michael P. Rice.
European Patent Office, Search Report dated Jun. 29, 2011 in European application No. 10252182.0-1243/2336881.
Intel Corporation, "Endianness White Paper," Nov. 15, 2004, pp. 1-22.
Wikipedia, "Type System," Dec. 13, 2009, pp. 1-12.
Wikipedia, "Endianness," Dec. 14, 2009, pp. 1-8.
Wikipedia, "Type conversion," Nov. 17, 2009, pp. 1-3.
State Intellectual Property Office, P.R. China, Office Action issued Sep. 18, 2012 and Search Report in Chinese application No. 201010621047.1.
Cutler, Richard, et al., "AIX 5L Porting Guide" IBM Redbooks, Jul. 2001, pp. 33-42, First Edition, International Business Machines Corporation, Austin, Texas.
Japanese Patent Office, Office Action mailed Jan. 29, 2013 in Japanese application No. 2010-247123.

* cited by examiner

*Primary Examiner* — Ted T Vo
(74) *Attorney, Agent, or Firm* — Trop, Pruner & Hu, P.C.

(57) ABSTRACT

An embodiment of the invention includes code, such as a compiler, that enables byte order dependent code to execute on opposite byte order dependent architectures or systems. The compiler analyzes source code and produces diagnostic reports that indicate where source code changes are desirable to produce "endian neutral" source code versions that are compatible with opposite byte order dependent architectures or systems. Such source code changes may be desirable for code portions that will produce implicit byte order changes or byte order border crossings. The modified source code that is generated may include the semantics of the desired endian conversion, as opposed to generated executable code that includes proper endian formats but which may limit the architectures to which the code is applicable.

16 Claims, 3 Drawing Sheets

Diagnostic Report #1(DR1)          205

1) Compiler creates symbol table to store information on data structures defined in the source code.
2) For all data structures, x, in the symbol table
   a) If x contains a bit field and not marked with no diagnostic attribute, identify X in DR1.
   b) If x contains a union with fields of different sizes and not marked with no diagnostic attribute, identify X in DR1.

Diagnostic Report #2 (DR2)          225

1) Compiler creates a control flow graph containing an intermediate language representation of the source code including assignments.
2) Compiler creates a new header file and opens same for writing.
3) For all assignments, x, in the intermediate language representation:
   a) If the byte order of the type on the left hand side of the assignment does not match the byte order of the type on the right hand side of the assignment then
      i) Identify assignment X in DR2 and describe the issue and source location.
      ii) Add to the header file a definition for a conversion function that employs a byte swap function to convert from the type on the right hand side to the type on the left hand side.

Example:
__Assume the following code:
  int __attribute__((bigendian)) x;
  int __attribute__((littleendian)) y;
  y = x;

Diagnostic displayed:
  Byte order boundary crossed in assignment of bigendian int to littleendian int (<filename>, <line number>

Conversion function added:
  __attribute__((littleendian)) int convert_be_int_to_le_int(__attribute__((bigendian)) int value) {
  return <architecture specific byteswap function> value;
}

Diagnostic Report #3 (DR3)          255

1) Compiler issues diagnostics when assignments or casts result in an implicit or explicit byte order conversion.
2) Compiler provides a conversion routine for the programmer to use after the programmer has exposed the byte order change.

FIG. 2C

METHODS AND APPARATUSES FOR ENDIAN CONVERSION

BACKGROUND

Byte endianess is an attribute of data storage and retrieval. Big endian data may be stored in memory in opposite byte order from little endian data. Little endian data may be stored with the least significant byte in the lowest memory byte address while big endian data may be stored with the most significant byte in the lowest memory byte address. Big and little endian variables having the same value are identical in CPU registers but may have differing order in memory.

Source code that is written using one byte endianess convention may not be executed on a platform using another endianess convention without recognizing the differing order of how some data are stored in memory. For example, it may be desirable to preserve endian byte ordering within data written to or read from outside a program.

Endian conversion, which may be performed using several techniques, may be used to execute code written in one endianess convention on a computer system platform of another endianess convention. First, a programmer may use a manual endian conversion technique to manually analyze code and attempt to detect where byte order dependencies exist. The programmer may then insert, for example, byteswap (i.e., endian flip) instructions to address the identified dependencies. However, it may be difficult to manually find these dependency areas. Second, with a bi-endian compiler a programmer may designate the byte order of code regions. The bi-endian compiler then automatically inserts byteswaps into a compiled executable that can execute with opposite byte order semantics. However, the use of such a unique compiler may limit the platforms to which the source code is applicable. Third, binary translation may enable execution of executables targeted to a different architecture using dynamic translation of instructions from one instruction set to another while maintaining byte order semantics. However, such translations can be slow and affect system performance.

BRIEF DESCRIPTION OF THE DRAWINGS

Features and advantages of embodiments of the present invention will become apparent from the appended claims, the following detailed description of one or more example embodiments, and the corresponding figures, in which:

FIGS. 2A, 2B, and 2C include pseudo code for methods in embodiments of the invention.

DETAILED DESCRIPTION

In the following description, numerous specific details are set forth. However, it is understood that embodiments of the invention may be practiced without these specific details. Well-known circuits, structures and techniques have not been shown in detail to avoid obscuring an understanding of this description. References to "one embodiment", "an embodiment", "example embodiment", "various embodiments" and the like indicate the embodiment(s) so described may include particular features, structures, or characteristics, but not every embodiment necessarily includes the particular features, structures, or characteristics. Further, some embodiments may have some, all, or none of the features described for other embodiments. Also, as used herein "first", "second", "third" describe a common object and indicate that different instances of like objects are being referred to. Such adjectives are not intended to imply the objects so described must be in a given sequence, either temporally, spatially, in ranking, or in any other manner.

An embodiment of the invention includes code, such as a compiler, that enables byte order dependent code to execute on opposite byte order dependent architectures or systems. The compiler analyzes code (e.g., source code) and produces diagnostic reports that indicate where source code changes are desirable to produce "endian neutral" source code versions and the like that are compatible with opposite byte order dependent architectures or systems. For example, programmers may designate a desired byte order for specific code regions in source code and the compiler may then help the programmers make the changes necessary to enact those desired endian configurations. The modified source code that is generated may include the semantics of the desired endian conversion, as opposed to generated executable code that includes proper endian formats but which may limit the architectures to which the code is applicable. Also, embodiments of the invention may produce endian swap instructions in modified source code that can be compiled into native executable code, which executes faster than translated executables that include byteswaps imposed during translations.

For clarity many example embodiments discussed herein address a compiler (e.g., C/C++ compiler) and its application to source code and swapping between big and little endian conventions, but embodiments of the invention are not necessarily so limited. For example, while embodiments include analytic code, such as an analytic tool included in a compiler, other embodiments may include analytic code included in a static analysis checking tool. Furthermore, endian conversion is often discussed herein with regard to byteswap instructions but various embodiments are not necessarily limited to employing any specific type of instructions to perform or promote endian conversion.

Figure 1:
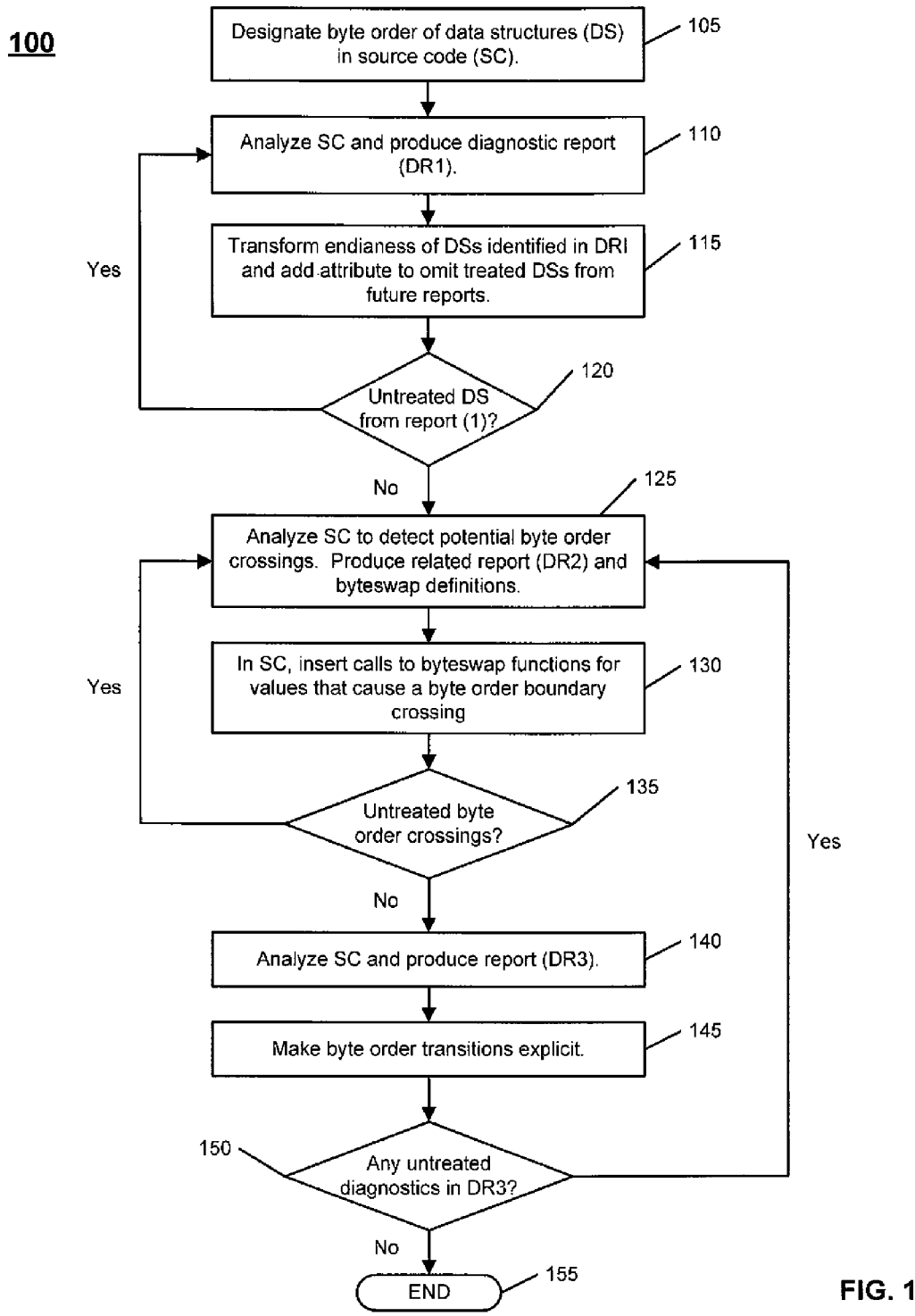
FIG. 1 is a block diagram of a method in an embodiment of the invention.

FIG. 1 is a block diagram of a method 100 in one embodiment of the invention. In block 105, a programmer may use a program to designate source code portions (e.g., data structures) that he or she desires to access data with big or little endian semantics. Some source code portions or sections may be designated as originally big endian but intended to be converted to little endian (and vice versa). Other code sections may be designated as originally big endian and may be further designated as needing to remain big endian (e.g., Internet Engineering Task Force (IETF) protocol headers).

For example, there may be constraints on portions of the code such as code that was developed for a big endian architecture. However, a user may want to port the code to run on little endian architectures. When the port occurs, certain libraries may be included in the modified code, such as libraries that assume little endian conventions are in place (and/or other libraries that assume big endian conventions are in place). Code portions in the unmodified code that will interact with these libraries in the modified code may be designated as code that may use an endian convention change in the modified code. The code portions may alternatively be designated as code where it is desirable for the code to have its endian convention maintained in the modified code. Thus, the programmer may make these designations using, for example, compiler language constructs (e.g., command lines, pragmas, and/or attributes).

In block 110, the compiler may use a system processor to analyze the source code and its designated code portions to produce an analysis, such as a first diagnostic, which can be stored in system memory. A diagnostic may include, for example, an instrument to draw a programmer's attention to certain matter. A diagnostic may include a report, message, indicator, identifier, and the like. In one embodiment a diagnostic report (DR1) may flag or identify code portions, such as data structures, where manual byte order conversion may be desirable. Such data structures may contain, for example, bit fields of different sizes and/or unions with fields of different sizes, where byte order analysis may be desirable. Embodiments of DR1 may document what byte order the compiler is presently associating with various unions to help the developer confirm the "original" byte order of the union.

In block 115, the programmer may manually transform the portions (e.g., data structures) highlighted in DR1 into their respective opposite byte order representations. In an embodiment of the invention, he or she may add a new language construct (e.g., attribute) to the source code to prevent the compiler from listing the already transformed structures (or structures already analyzed but which the programmer elected not to transform) in DR1s that may be issued in future compilations.

FIG. 2A includes pseudo code 205 in one embodiment of the invention related to DR1 reports. To generate DR1, the compiler may create a symbol table that stores information on various data structures defined in the source code. A symbol table may include a list of all identifiers encountered when a program is compiled (or assembled), their locations in the program, and their attributes, such as variable, routine, and the like. Then, for some or each data structure (x) included in the symbol table, the compiler may identify the data structure in DR1 if the structure contains, for example, a bit field because the presence of a bit field may indicate to the programmer the potential for endian format issues. As another example, if data structure x contains a union with fields of different sizes, the compiler may identify the data structure in DR1. The compiler may also search for indications that the particular code portion has already been analyzed in a previous iteration. In such a case, the already analyzed portion may not be noted in the present DR1.

Returning to FIG. 1, in block 120, the method returns to block 110 and repeats blocks 110 and 115 until no diagnostics are listed in DR1. After no diagnostics are untreated (or determined that they will not be treated), in block 125 an embodiment analyzes the source code and produces additional analysis, such as a second diagnostic report (DR2).

DR2 may identify code operations on data that result in crossing a byte order boundary. For example, on a little endian architecture a byte order boundary may be crossed upon (a) a load of a big endian value into a register before an arithmetic operation takes place upon the value or (b) upon an assignment of a value with big endian byte order to a variable stored in little endian byte order. In addition, DR2 may include an implementation file (e.g., header file) with definitions of byteswap functions, such as one definition for each type detected in DR2.

In block 130, the programmer may use DR2 and its definitions to manually insert calls to byteswap functions, which correspond to particular variable types identified in DR2, at locations in the source code near references to the variables. This may have the effect of converting the value, which may have caused a byte order boundary crossing if left untreated, to its opposite byte order representation. In one embodiment, upon recompilation the compiler may not emit a diagnostic in a future DR2 as long as the correct byteswap function was employed.

FIG. 2B includes pseudo code 225 in one embodiment of the invention related to DR2 reports. The compiler may create a control flow graph containing an intermediate language representation of the source code including assignments. The compiler may then create a new header file and open the same. For some or all assignments (x) in the intermediate language representation, the compiler may do the following. For example, if the byte order of the type on the left hand side of the assignment does not match the byte order of the type on the right hand side of the assignment then the compiler may identify assignment (x) in DR2 and describe the issue and source code location. The compiler may also add to the open header file a definition for a conversion function that employs a byteswap function to convert from the type on the right hand side of the assignment to the type on the left hand side of the assignment (e.g., to convert from big to little endian).

Returning to FIG. 1, in block 135, the method returns to block 125 and repeats blocks 125 and 130 until no diagnostics are listed in DR2. After all diagnostics have been treated (or determined that they will not be treated), in block 140 an embodiment analyzes the source code and produces additional analysis, such as a third diagnostic report (DR3).

DR3 may include diagnostics that alert the programmer when an explicit or implicit byte order conversion is present. For example, DR3 diagnostics may alert the programmer when casts result in an explicit byte order conversion and/or assignments result in an implicit byte order conversion.

An explicit conversion occurs when, for example, a programmer explicitly writes a cast expression such as:

```
{
    int beint;
    void *p = (void*)&beint; // converts from big-endian int pointer
    to void pointer
}
```

Here, the source code contains a cast from one endian type to a void pointer. Another example of an explicit conversion that DR3 may identify includes a cast including a programmer-specified data conversion from one data type to another, such as a conversion from integer to floating point. As another example, source code may have unions containing pointers to objects of different sizes. Furthermore, source code may include pointers that cast to reference data of different sizes. DR3 may note these explicit conversions.

The programmer may desire that the byte order, which was specified by the user as the original byte order for the referenced data, remain unchanged. In this case, the compiler may produce a diagnostic in DR3 if the byte order has changed and the diagnostic may then, for example, be manually addressed by insertion of byteswaps. In one embodiment, detection of such unions may have been unaddressed in DR1 because DR1 in such an embodiment catches or identifies unions with fields of different sizes but not unions with pointers that point to data of different sizes.

In contrast to an explicit conversion, an implicit conversion occurs when, for example, a pointer to a value of one type is passed to a function that expects a pointer to a value of a different type. In this context the data types differ with regard to byte order. The following addresses some other implicit conversions that DR3 may identify. For example, an implicit conversion may be similar to explicit conversions addressed above but may not use a cast expression (e.g., void*p=&beint; // converts from big-endian int pointer to void pointer).

As another example of an implicit conversion that DR3 may diagnose, source code may include a union containing an array as a field that is not declared in an endian neutral way.

After DR3 brings this to the programmer's attention, such an array may be converted to having named fields to make conversions therein more explicit. Also, access to such arrays may be flagged in DR3 because the correct offset for an access to an array may depend upon byte order. In one embodiment, detection of such unions including the aforementioned arrays may have been passed through and not addressed in DR1.

Following is another example of an implicit conversion that may be diagnosed by DR3:

```
{
    void func(int *be__int);
    le__int x;
    func(&x);
}
```

In this case, the address of a little endian value may be passed to a function expecting to operate on something in big endian format. As far as the function is concerned, the pointed to value is big endian and thus x has been implicitly converted (e.g., the conversion is implied).

In cases involving implicit conversions identified by DR3, the programmer may change (block 145) source code having an implicit byte order conversion into modified source code that has an explicit byte order change. He or she may then apply techniques described herein to insert code (e.g., byteswaps) to handle the explicit byte order changes.

Changes regarding explicit or implicit conversions may be made after DR3 is received or after the method, or portions thereof, are repeated to produce later versions of DR1, DR2, and/or DR3. In some embodiments, however, some reports (e.g., DR1) may not be generated a second time. Also, in an embodiment attributes or casting sequences may be available to suppress DR3 diagnostics for constructs that the programmer determines to be safe, even when the compiler is unable to make that determination.

FIG. 2C includes pseudo code 255 in one embodiment of the invention related to DR3 reports. As addressed with several examples above, diagnosed assignments may indicate implicit conversions are present. Also, diagnosed casts may indicate explicit conversions are present. The programmer may elect to make implicit conversions into explicit conversions. Furthermore, the programmer may be presented with options (e.g., byteswap options) to convert code according to his or her desired byte convention in the modified source code.

Returning to FIG. 1, in block 150, the method returns to block 125 and repeats blocks 125 though 145 to produce DR2 and DR3 for the modified source code until fewer or no diagnostics are listed in DR3. After some or all diagnostics have been treated (or determined that they will not be treated), in block 155 the method ends.

As the declared byte order changes, the point at which byteswaps may be desirable may change. Thus, the programmer may repeat method 100, or portions thereof, refining the modified source program to contain the desired instructions (e.g., byteswap instructions) so it may operate with systems of opposite endian convention.

Thus, embodiments of the invention may request the programmer insert code (e.g., byteswaps) as opposed to a compiler that automatically inserts code (e.g., byteswaps) and compiles the code. This may produce source code which can be compiled using numerous standard compilers. Embodiments of the invention may allow a programmer to denote a set of definitions. The code (e.g., compiler) may then guide the user to the set of values interacting with these definitions (e.g., through data flow) where endian format changes are desirable. This may allow the user to efficiently modify source code to create another version of the source code or the like that may be used with various architectures.

Figure 3:
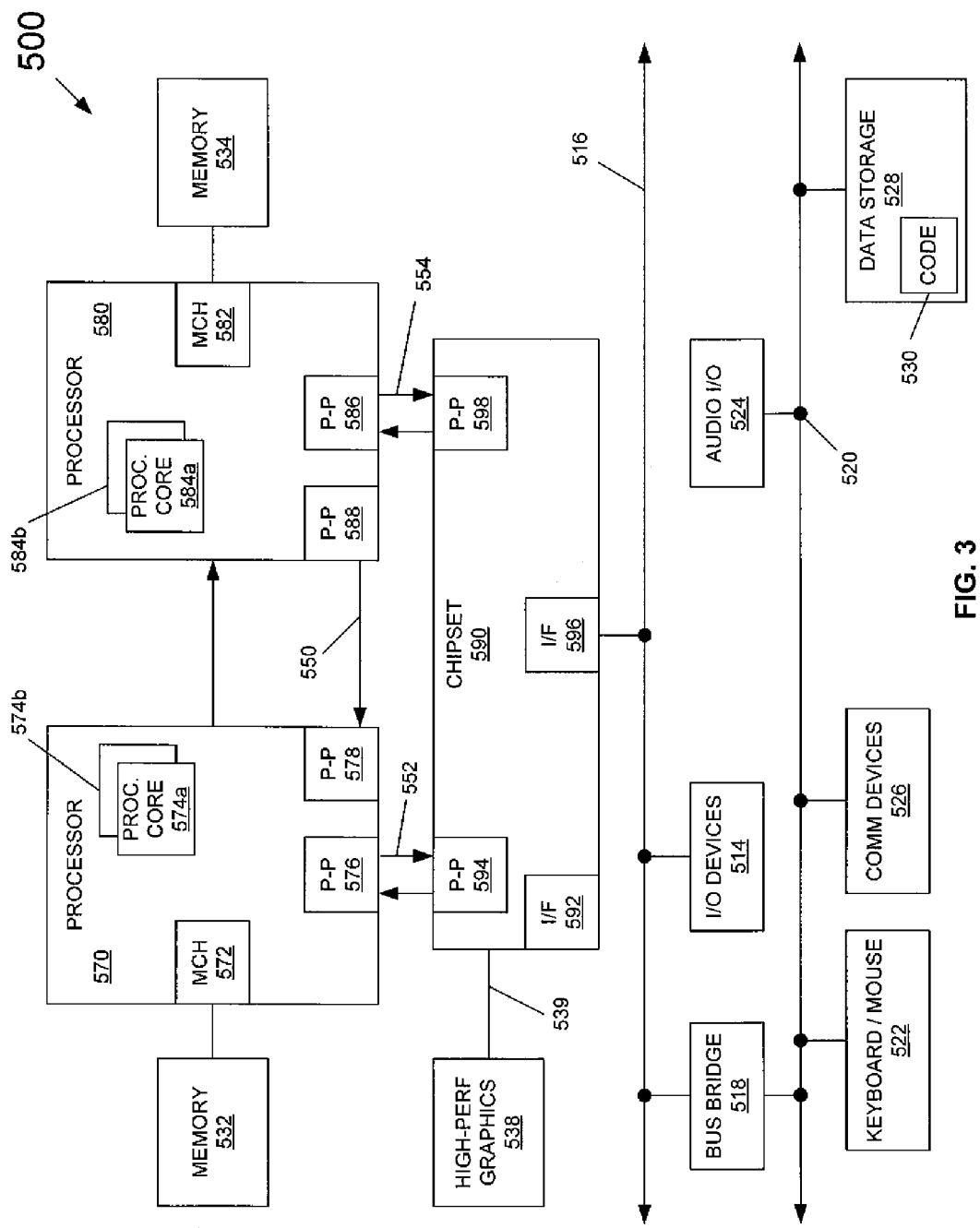
FIG. 3 is a system block diagram for use with an embodiment of the invention.

Embodiments may be implemented in many different system types. Referring now to FIG. 3, shown is a block diagram of a system in accordance with an embodiment of the present invention. Multiprocessor system 500 is a point-to-point interconnect system, and includes a first processor 570 and a second processor 580 coupled via a point-to-point interconnect 550. Each of processors 570 and 580 may be multicore processors, including first and second processor cores (i.e., processor cores 574a and 574b and processor cores 584a and 584b), although potentially many more cores may be present in the processors. The term "processor" may refer to any device or portion of a device that processes electronic data from registers and/or memory to transform that electronic data into other electronic data that may be stored in registers and/or memory.

First processor 570 further includes a memory controller hub (MCH) 572 and point-to-point (P-P) interfaces 576 and 578. Similarly, second processor 580 includes a MCH 582 and P-P interfaces 586 and 588. MCHs 572 and 582 couple the processors to respective memories, namely a memory 532 and a memory 534, which may be portions of main memory (e.g., a dynamic random access memory (DRAM)) locally attached to the respective processors. First processor 570 and second processor 580 may be coupled to a chipset 590 via P-P interconnects 552 and 554, respectively. Chipset 590 includes P-P interfaces 594 and 598.

Furthermore, chipset 590 includes an interface 592 to couple chipset 590 with a high performance graphics engine 538, by a P-P interconnect 539. In turn, chipset 590 may be coupled to a first bus 516 via an interface 596. Various input/output (I/O) devices 514 may be coupled to first bus 516, along with a bus bridge 518, which couples first bus 516 to a second bus 520. Various devices may be coupled to second bus 520 including, for example, a keyboard/mouse 522, communication devices 526, and data storage unit 528 such as a disk drive or other mass storage device, which may include code 530, in one embodiment. Further, an audio I/O 524 may be coupled to second bus 520.

Embodiments may be implemented in code and may be stored on a storage medium having stored thereon instructions which can be used to program a system to perform the instructions. The storage medium may include, but is not limited to, any type of disk including floppy disks, optical disks, optical disks, solid state drives (SSDs), compact disk read-only memories (CD-ROMs), compact disk rewritables (CD-RWs), and magneto-optical disks, semiconductor devices such as read-only memories (ROMs), random access memories (RAMs) such as dynamic random access memories (DRAMs), static random access memories (SRAMs), erasable programmable read-only memories (EPROMs), flash memories, electrically erasable programmable read-only memories (EEPROMs), magnetic or optical cards, or any other type of media suitable for storing electronic instructions.

Embodiments of the invention may be described herein with reference to data such as instructions, functions, procedures, data structures, application programs, configuration settings, code, and the like. When the data is accessed by a machine, the machine may respond by performing tasks, defining abstract data types, establishing low-level hardware contexts, and/or performing other operations, as described in greater detail herein. The data may be stored in volatile and/or non-volatile data storage. For purposes of this disclosure, the terms "code" or "program" cover a broad range of components and constructs, including applications, drivers, processes, routines, methods, modules, and subprograms. Thus, the terms "code" or "program" may be used to refer to any collection of instructions which, when executed by a processing system, performs a desired operation or operations. In addition, alternative embodiments may include processes that use fewer than all of the disclosed operations, processes that use additional operations, processes that use the same operations in a different sequence, and processes in which the individual operations disclosed herein are combined, subdivided, or otherwise altered.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A method executed by at least one processor comprising:
designating a first endian format for a first source code portion and a second endian format for a second source code portion;
generating, using a processor coupled to a memory, a first diagnostic report based on determining, using the processor, whether the first code portion will produce a byte order boundary crossing;
generating a second diagnostic report based on determining, using the processor, whether the second code portion will produce an implicit byte order conversion when executed in response to the designation of the second code portion; and
storing the first and second diagnostic reports in the memory;
wherein determining whether the first code portion will produce a byte order boundary crossing is based on determining: (a) a variable, included in the first code portion, is formatted with the first endian format, and (b) the first code portion includes code that will assign a value, previously declared as being formatted with an endian format opposite the first endian format, to the variable.

2. The method of claim 1 including:
generating a third diagnostic report based on determining whether a third source code portion includes one of a bit field and a union that includes differently sized fields; and
storing the third diagnostic report in the memory.

3. The method of claim 1 including determining whether the second code portion will produce an implicit byte order conversion when executed based on determining, using the processor, the second code portion includes a union data structure.

4. The method of claim 1 including determining whether the second code portion will produce an explicit byte order conversion when executed based on the designation of the second code portion.

5. The method of claim 4 including determining whether the second code portion will produce an explicit byte order conversion when executed based on determining, using the processor, the second code portion includes a cast instruction.

6. The method of claim 1 including generating modified source code based on the first and second diagnostic reports, wherein the first endian convention is opposite the second endian convention.

7. An article comprising a non-transitory medium storing instructions that enable a processor based-system to:
receive user input designating a first endian format for a first portion of source code and a second endian format for a second portion of source code;
determine whether the first portion will produce a byte order boundary crossing when executed;
determine whether the second portion will produce an implicit byte order conversion when executed in response to the designation of the second code portion;
generate a first diagnostic report based on determining whether the first portion will produce a byte order boundary crossing when executed; and
generate a second diagnostic report based on determining whether the second portion will produce an implicit byte order conversion when executed;
wherein determining whether the first portion will produce a byte order boundary crossing is based on determining: (a) a variable, included in the first portion, is formatted with the first endian format, and (b) the first portion includes code that will assign a value, previously declared as being formatted with an endian format opposite the first endian format, to the variable.

8. The article of claim 7 further storing instructions that enable the processor-based system to generate a third diagnostic report based on determining whether a third portion of the source code includes one of a bit field and a union including differently sized fields.

9. The article of claim 7 further storing instructions that enable the processor-based system to determine whether the second portion will produce an implicit byte order conversion when executed based on the second portion including code that will cause an endian conversion without use of a cast instruction, the code including one of (a) a pointer to a value having an endian format being passed to a function having an opposite endian format, and (b) a void pointer.

10. The article of claim 7 further storing instructions that enable the processor-based system to determine whether the second portion will produce an implicit byte order conversion when executed based on the second portion including a union that (a) includes an array, and (b) will cause an endian conversion.

11. The article of claim 7 further storing instructions that enable the processor-based system to determine whether the second portion will produce an explicit byte order conversion when executed based on the designation of the second portion, wherein the report includes a prompt.

12. The article of claim 7 further storing instructions that enable the processor-based system to determine whether the second portion will produce an explicit byte order conversion when executed based on the second portion including a cast instruction.

13. The article of claim 7 further storing instructions that enable the processor-based system to generate the first and second diagnostic reports in non-executable form.

14. An apparatus comprising:
a processor, coupled to a first memory, to:
(1) determine whether a first portion of source code will produce a byte order boundary crossing when executed;
(2) determine whether a second portion of the source code will produce an implicit byte order conversion when executed;
(3) generate a first diagnostic report based on determining whether the first portion will produce a byte order boundary crossing when executed; and (4) generate a second diagnostic report based on determining whether the second portion will produce an implicit byte order conversion when executed;

wherein determining the first portion will produce a byte order boundary crossing is based on determining: (a) a variable, included in the first portion, is formatted with a first endian format, and (b) the first portion includes code that will assign a value, previously declared as being formatted with an endian format opposite the first endian format, to the variable.

15. The apparatus of claim 14, wherein the processor is to generate a third diagnostic report based on determining whether a third portion of the source code includes one of a bit field and a union.

16. The apparatus of claim 14, wherein the processor is to determine whether the second portion will produce an implicit byte order conversion when executed based on the second portion including code that will cause an endian conversion without use of a cast instruction.

* * * * *